United States Patent [19]

Röchling et al.

[11] 4,180,575
[45] Dec. 25, 1979

[54] TRIAZOLIDINO-PYRIDAZINE-DIONES

[75] Inventors: Hans Röchling, Bad Soden am Taunus; Burkhard Sachse, Kelkheim; Hans Gattner, Bad Nenndorf, all of Fed. Rep. of Germany

[73] Assignee: Hoechst Aktiengesellschaft, Frankfurt am Main, Fed. Rep. of Germany

[21] Appl. No.: 780,244

[22] Filed: Mar. 22, 1977

[51] Int. Cl.[2] ............... C07D 487/04; A01N 9/22; A61K 31/50
[52] U.S. Cl. ................................. 424/250; 544/198; 544/236; 424/249
[58] Field of Search .............. 424/250; 260/250 AC; 544/236

[56] References Cited
FOREIGN PATENT DOCUMENTS
318635 11/1974 Austria .

OTHER PUBLICATIONS
Novikov, Chem. Abs. 68, 29687u, (1967).
Makarov et al., Chem. Abs. 68, 29688v, (1967).
Roechling, Hans et al., Chem. Abs., 87, 39525w, (1977).

*Primary Examiner*—Mark L. Berch
*Attorney, Agent, or Firm*—Curtis, Morris & Safford

[57] ABSTRACT

Triazolidino-pyridazine-diones of the formula (I)

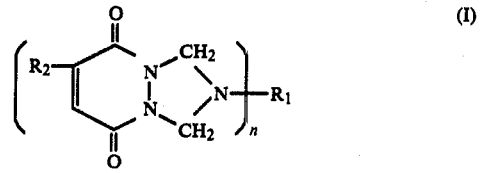

in which n represents an integer which is 1 or above, preferably the integers 1, 2 or 3,
$R_1$ is n-valent organic radical and
$R_2$ is hydrogen or the methyl group,
their preparation by reacting pyridazine-diones of the formula (II)

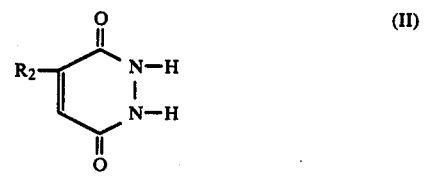

with primary amines of the formula (III)

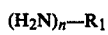

and formaldehyde, n, $R_1$ and $R_2$ being defined as in formula (I) above,
as well as their use as fungicidal and bactericidal agents.

8 Claims, No Drawings

TRIAZOLIDINO-PYRIDAZINE-DIONES

The present invention relates to triazolidino-pyridazine-diones.

The present invention provides triazolidino-pyridazine-diones of the formula (I)

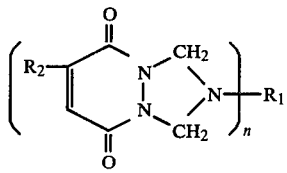
(I)

in which n represents an integer which is 1 or above, preferably the integers 1, 2 or 3, $R_1$ is a n-valent organic radical and $R_2$ is hydrogen or the methyl group, and wherein, (1) if n equals 1, $R_1$ is an optionally branched alkyl radical having 1 to 18 carbon atoms, especially 1 to 12 carbon atoms, which may also be substituted, an optionally substituted cycloalkyl radical having 5 to 8 carbon atoms, the norbornylmethyl radical, a hydroxyalkyl, alkoxyalkyl or alkylmercaptoalkyl radical having 2 to 8 carbon atoms, especially 2 to 6 carbon atoms, a phenyl or benzyl radical which may also be substituted, especially by halogen, halogenoalkyl, nitro, nitrile, $(C_1-C_4)$-alkyl or $(C_1-C_4)$-alkoxy groups, or, (2) if n equals 2, $R_1$ is a bivalent, optionally branched or cyclic alkylene radical having 1 to 36 carbon atoms, preferably 1 to 12, especially 1 to 6 carbon atoms, which may also be substituted, especially by $(C_1-C_4)$-hydroxyalkyl, $(C_1-C_4)$-alkoxyalkyl, $(C_1-C_4)$-alkylmercaptoalkyl groups or halogen, a bivalent aromatic or araliphatic or heterocyclic radical having up to 36 carbon atoms, preferably up to 24, especially up to 12 carbon atoms, which may also be substituted, especially by $(C_1-C_4)$-hydroxyalkyl, $(C_1-C_4)$-halogenoalkyl, $(C_1-C_4)$-alkoxyalkyl, $(C_1-C_4)$-alkylmercaptoalkyl, $(C_1-C_4)$-alkyl, nitro, nitrile groups or halogen, or (3) if n equals 3, $R_1$ is a trivalent, optionally branched or cyclic aliphatic radical having 3 to 36 carbon atoms, especially 3 to 9 carbon atoms, which may also be substituted, especially by $(C_1-C_4)$-hydroxyalkyl, $(C_1-C_4)$-alkoxyalkyl, $(C_1-C_4)$-alkylmercaptoalkyl groups or halogen, a trivalent aromatic or araliphatic or heterocyclic radical having up to 36 carbon atoms, preferably up to 24, especially up to 12 carbon atoms, which may also be substituted, especially by $(C_1-C_4)$-hydroxyalkyl, $(C_1-C_4)$-halogenoalkyl, $(C_1-C_4)$-alkoxyalkyl, $(C_1-C_4)$-alkylmercaptoalkyl, $(C_1-C_4)$-alkyl, nitro and nitrile groups or halogen.

The invention further provides a process for the preparation of compounds of the formula (I), which comprises reacting pyridazine-diones of the formula (II)

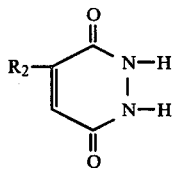
(II)

with primary amines of the formula (III)

$(H_2N)_n-R_1$ (III)

and formaldehyde, n, $R_1$ and $R_2$ being defined as in formula (I) above.

A preferred embodiment of the process consists in suspending or dissolving the pyridazine-dione (II) in a solvent, adding from 1 to 2 times the required molar amount of amine, preferably 1.2-fold to 1.7-fold the molar amount thereof, and thereafter adding, while stirring, 2 to 4 times the molar amount, preferably 2.5-fold to 3.5-fold the molar amount, of formaldehyde, preferably in the form of an aqueous formaldehyde solution. The reaction is advantageously carried out at a temperature in the range of from 0° to +80° C., especially from +20° to +40° C., the temperature range not being critical, however. Manually, the reaction product is dissolved and may in this solution be separated from undissolved pyridazine-dione which might still be present. By subsequently evaporating this solution and treating the residue with an inert solvent, such as benzine, or by reprecipitating the product, for example from a mixture of methylene chloride and benzine, the triazolidino-pyridazine-dione can be isolated in its pure form.

Even in cases where an amount of formaldehyde is used which is less than the one specified, the reaction yields the final product (I).

For some application purposes the substances of the invention are used in an aqueous solution, so that it may be advantageous in these cases to prepare said substances directly in water as solvent. For this purpose it is important, naturally, to use the pyridine-dione (II), the amine and the formaldehyde in the appropriate molar ratios. After the reaction has been completed, the reaction solution may be used directly, as it no longer contains any excess starting materials.

Besides the amines used in the Examples, the following amines, diamines and triamines are particularly suitable starting compounds according to the invention, for example: Ethylamine, propylamine, isopropylamine, isobutylamine, isoamylamine, hexylamine, isohexylamine, heptylamine, isoheptylamine, octylamine, isooctylamine, nonylamine, decylamine, undecylamine, tridecylamine, pentadecylamine, hexadecylamine, octadecylamine, cyclopentylamine, cycloheptylamine, cyclooctylamine, cyclohexylamine, 2-amino-2-methyl-1-propanol, 2-amino-2-ethyl-propanediol-1,3, 2-hydroxyethylamine, 2-hydroxypropylamine, 4-hydroxybutylamine, 5-hydroxypentylamine, 4-methoxybutylamine, 5-methoxypentylamine, 4-ethoxy-butylamine-5-ethoxypentylamine, 3-propoxypropylamine, 4-propoxybutylamine, 5-propoxypentylamine, 3-methylmercaptopropylamine, 4-methylmercapto-butylamine, 3-propylmercapto-propylamine, 4-propylmercapto-butylamine, ω,ω'-diaminodialkylether, ω,ω'-diaminodialkylthioether, methylcyclohexylamine, 1,1-dimethylpropine-2-ylamine, 1,1-diethylpropine-2-ylamine, halogenoaniline, nitroaniline, toluidine, anisole, aminobenzonitrile; methylenediamine, ethylene-diamine, propylene-diamine, butylene-diamine, hexamethylene-diamine, 1-amino-2-aminomethyl-3,3,5-trimethylcyclopentane; triaminoalkanes, triaminoisononane, triaminohexahydrotriazine, triaminotetrahydrotriazine, triaminodihydrotriazine, 2,4,6-triamino-1,3,5-triazine (melamine) and 1,2,3-triaminopropane.

Furthermore, all soluble primary amines, diamines, triamines, oligoamines or polyamines may be used advantageously.

As solvents for the reaction there may be used, for example, water or moderately to slightly polar solvents, preferably those having a low boiling point, such as methylene chloride, chloroform, carbon tetrachloride, benzene; ethers, such as diethylether, diisopropylether and tetrahydrofuran; esters, such as methyl acetate and ethyl acetate or ketones, for example acetone or methylethyl ketone. Use is made preferably of water, chloroform or methylene chloride.

The preparation of the pyridazine-diones (II) used as starting compounds, as well as the preparation of the amines (III) required for the reaction, are already known in the literature.

The formaldehyde is used preferably as an aqueous formalin solution, but there may also be used other products which split off formaldehyde under the reaction conditions, such as, for example, paraldehyde or trioxane. The compounds of the general formula (I) show an excellent fungicidal and bactericidal action in the technical field as well as in plant protection. They are thus suitable for the preservation of lacquers, dyes, glues, paints, thickeners, sealing compounds, drilling and cutting oils, for the protection of wood and paper products as well as of textiles, and also for the use as plant protective agents.

For example, the compounds of the formula (I) with lower alkyl radicals $R_1$ have generally a good to limited water-solubility, with the solubility in water decreasing with the increase of the chain length of $R_1$, and the solubility in organic solvents generally increasing. Substitutions to $R_1$ by polar groups improve the water-solubility. The tris-triazolidino-pyridazine-dione obtained with melamine, for example, is sparingly soluble in water and is therefor excellently suitable as fungicidal agent for paints, especially for paints which are exposed to weather influences.

The compounds show a very good action against fungi, for example:
*Aureobasidium pullulans,*
*Aspergillus flavus,*
*Aspergillus niger,*
*Aspergillus orycae,*
*Alternaria consortiale,*
*Chaetomium globosum,*
*Coniophora puteana,*
*Geotrichum candidium,*
*Lenzites abietina,*
*Merulius lacrimans,*
*Penicillium funiculosum,*
*Penicillium janthinellum,*
*Penicillium vermiculatum,*
*Pencillium wortmanni,*
*Poria monticola,*
against genuine mildew types, *Phytophthora infestans, brown rust of wheat, Plasmopara viticola, Cercospora betae* and *Cladosporium fulvum* as well as against *Pytium ultimum, Ustilago avenae* and *Phoma betae;* against Gram-positive and Gram-negative bacteria, for example:
*Aerobacter aerogenes,*
*Bacillus subtilis,*
*Escherichia coli,*
*Proteus vulgaris* and
*Pseudomonas aeruginosa;*
as well as against yeasts, for example *Saccharomyces cerevisiae.*

For the use as technical bactericidal and fungicidal agents the compounds are used as such or in combination with other biocidal agents, predominantly in the form of aqueous solutions or dispersions or also directly as additives to coating and painting substances.

For the use as plant protective agents they may be formulated as dusts, wettable powders, dispersions, emulsion concentrates or granules. Their content of total active ingredient is in these cases in the range of from 10 to 90% by weight. Besides, they contain the common adhesive, wetting and dispersing agents, fillers and carriers. They may also be mixed with other fungicidal agents with which they form compatible mixtures.

As carriers there may be used mineral substances, such as aluminum silicates, aluminas, kaolin, chalks, siliceous chalks, talc, kieselguhr or hydrated silicic acid, or preparations of these mineral substances with special additives, for example chalk lubricated with sodium stearate.

As carrier substances for liquid formulations there may be used all common and appropriate solvents, for example, toluene, xylene, diacetone alcohol, cyclohexanone, isophorone, benzines, paraffin oils, dioxan, dimethylformamide, dimethylsulfoxide, ethyl acetate, tetrahydrofuran, chlorobenzene, and others, as well as water.

As adhesives there may be mentioned glue-like cellulose products or polyvinyl alcohols.

As wetting agents there may be used all appropriate emulsifiers, such as oxethylated alkyl phenols, salts of aryl- or alkylaryl-sulfonic acids, salts of oleoylmethyl-taurine, salts of oxethylated phenylsulfonic acids or soaps.

As dispersing agents there are suitable cellulose pitch (salts of lignin-sulfonic acid), salts of naphthalene-sulfonic acid, or salts of oleoylmethyltaurine.

As grinding auxiliaries there may be used appropriate inorganic or organic salts, such as sodium sulfate, ammonium sulfate, sodium carbonate, sodium bicarbonate, sodium thiosulfate, sodium stearate or sodium acetate.

The following Examples illustrate the invention.

(A) Examples of Preparation

EXAMPLE 1:

22.4 Grams (0.2 mole) of pyridazine-dione (maleic acid hydrazide) are suspended in 400 ml of methylene chloride, and 19.8 g (0.2 mole) of cyclohexylamine are added. 34.4 Milliliters (0.4 mole) of 35% aqueous formaldehyde solution are added dropwise. In the course of this process the temperature rises from 25° to 33° C.; subsequently the reaction mixture is continued to be stirred for 2 hours at 33° C.

Then the mixture is allowed to cool, and magnesium sulfate is added to the same for drying. (A separation of the aqueous layer is unfavorable, since the reaction product is water-soluble). After filtration the product is concentrated; the residue is an oil which is introduced, while stirring, into petroleum ether at a temperature in the range of from 80° to 110° C. By cooling or partial concentration at the rotary evaporator, a crystalline solid matter is obtained, which is filtered off with suction and dried.

Yield 37.9 g (80.5% of the theory), melting point 99° to 101° C.

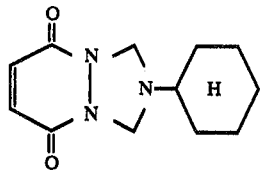

C₁₂H₁₇N₃O₂ mol. wt. 235.0

The substance is water-soluble.

Calculated: C 61.26%; H 7.24%; N 17.88% Found: C 60.9%; H 7.6%; N 17.8%
In the NMR spectrum there are found 2 olefinic protons, 4 CH₂-protons, 10 aliphatic protons (cyclohexyl) and 1 CH—N—proton.

The IR spectrum reveals an intensive carbonyl adsorption at 1620 cm⁻¹.

EXAMPLE 2:

56.0 Grams (0.5 mole) of pyridazine-dione are suspended in 1000 ml of methylene chloride, and 45.5 g (0.5 mole) of methylmercaptoethylamine are added. 85.5 Milliliters (1 mole) of 35% aqueous formaldehyde solution are added dropwise. In the course of this process the temperature rises from 25° to 32° C. The mixture is continued to be stirred for 30 minutes at 32° C., then it is allowed to cool, is dried over anhydrous magnesium sulfate, is subsequently filtered and concentrated. In this manner an oil is obtained as residue which crystallizes upon trituration with benzine at a temperature in the range of from 30° to 85° C.

The solid matter is filtered off with suction and dried.
Yield 83.0 g (73.5% of the theory), melting point 91° to 92° C.

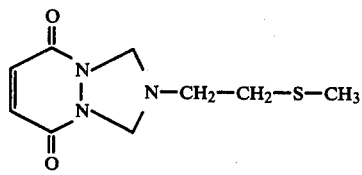

C₉H₁₃N₃O₂S mol. wt. 227.0

Calculated: C 47.58%; H 5.73%; N 18.5% Found: C 47.9%; H 6.0%; N 18.2%
In the infrared spectrum the compound shows a strong CO adsorption at 1612 cm⁻¹.

The substances of the formula (I)

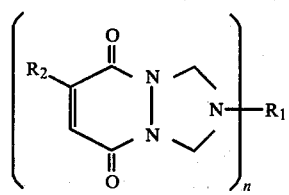

specified in the following Table have been prepared in a manner analogous to that of Examples (1) and (2).

Table

| Example | R₁ | R₂ | n | melt. point(°C.) |
|---|---|---|---|---|
| 3 | —CH₃ | H | 1 | 160–162 |
| 4 | —C₄H₉n | H | 1 | 55–56 |
| 5 | —(CH₂)₁₁—CH₃ | H | 1 | 80–82 |
| 6 | —(CH₂)₃—OH | H | 1 | 106–107 |
| 7 | —(CH₂)₃—OCH₃ | H | 1 | 93–94 |
| 8 | —C₉H₁₉iso | H | 1 | 91–92 |
| 9 | —C₁₈H₃₇ | H | 1 | 90–91 |
| 10 | —CH₂—(norbornyl) | H | 1 | 137–138 |
| 11 | —CH₂—C₆H₅ | H | 1 | 151 |
| 12 | phenyl | H | 1 | 206–208 |
| 13 | —C₄H₉n | CH₃ | 1 | non-distillable oil |
| 14 | —(CH₂)₁₁—CH₃ | CH₃ | 1 | 46 |
| 15 | —(CH₂)₃—OH | CH₃ | 1 | 98–101 |
| 16 | cyclohexyl | CH₃ | 1 | 118–120 |
| 17 | —CH₂—CH₂— | H | 2 | 157–158 |

EXAMPLE 18:

112 Grams (1 mole) of pyridazine-dione and 75 g (2 moles) of 3-aminopropanol are dispersed in 345 g of water. Subsequently 171 g (2 moles) of a 35% formaldehyde solution is introduced within 10 minutes. The mixture becomes clear and is heated to about 40° C. It is maintained at this temperature for about another hour, while stirring, and is then allowed to cool.

A 30% solution of N-3-hydroxypropyl-triazolidino-pyridazine-dione is obtained which is fast to storage also at 50° C. and which may be used in this form, for example, as a technical preservative.

EXAMPLE 19:

336 Grams (3 moles) of pyridazine-dione and 572 g (6 moles) of 35% aqueous formaldehyde are stirred at room temperature; then 126 g (1 mole) of melamine are added to this mixture, while heating to 60° C.

After about 30 minutes the suspension becomes at first clear, then the reaction product, tris-(triazolidino-pyridazine-dione)-triazine, precipitates as a thick precipitate. It is allowed to cool, is then filtered off with suction and dried at 80° C.

Yield:
526 Grams (98.5% of the theory)
Decomposition point:
245° C.

The substance is practically insoluble in water, it is particularly suitable, for example, as a fungicidal agent for paints which are exposed to extreme humidity.

In the following biological Examples the following comparative substances have been used:
A=Benzimidazole-carbamic acid-methylester+tetramethylthiuram-disulfide
B=Tetrahydro-3,5-dimethyl-2H-1,3,5-thiadiazine-2′-thione C = 1-Butylcarbamoyl-2-methoxycarbonylamino-benzimidazole
D = Manganese-ethylene-1,2-bis-dithiocarbamate
E = N-(trichloromethylthio)-phthalimide (B) Examples of Use

EXAMPLE I:

0.02 Milliliter each of a spore suspension of *Alternaria consortiale* was applied dropwise to a nutrient medium (biomalt agar) in Petri dishes, with the compounds of the preparation Examples (5) and (14) having been added previously to the agar in the liquid state in the concentrations given in Table I.

6 Days after the inoculation of the plates the diameter of the fungus colonies on the agar was measured, and the growth inhibition caused by the preparation was expressed in percent, calculated on the control (inoculated agar without the addition of (5) and (14) equalling 0% of inhibition).

As comparative agent there was used the substance A which was applied in the same concentrations as the claimed compounds.

Table I

| Compound acc. to | Inhibition of *Alternaria consortiale* in % with mg of active ingredient per liter of agar | | | |
|---|---|---|---|---|
| Example | 50 | 10 | 5 | 1 |
| 5 |  | 100 | 90 | 70 |
| 14 |  | 100 | 100 | 80 |
| A | 100 | 30 | 0 |  |

EXAMPLE II:

The tests were carried out and evaluated, as has been described in Example I. As test organism there was used *Aspergillus niger*.

Table II

| Compound acc. to | Inhibition of *Aspergillus niger* in % with mg of active ingredient per liter of agar | | | |
|---|---|---|---|---|
| Example | 50 | 10 | 5 | 1 |
| 5 |  | 100 | 80 | 60 |
| 14 |  | 100 | 90 | 70 |
| A | 100 | 50 | 20 |  |

EXAMPLE III:

0.02 Milliliter each of a bacteria suspension (mixture of *E. coli, Bacterium prodigiosum, Bacterium pyocyaneum*) was applied dropwise to a nutrient medium (standard-I-nutrient agar for bacteria) in Petri dishes, with the compounds of the preparation Examples (3), (2), (12), (10), (7), (6), (11), (16), (14), (13) and (15) having been added previously to the agar in the liquid state in the concentrations given in Table III.

The inoculated plates were evaluated after 4 days; in this process the growth inhibition was appraised as compared with the control (inoculated agar without addition of active ingredient equalling 0% of inhibition).

As comparative agents there were used commercial Hg-free products (A, B) which were applied in the same concentrations as the claimed compounds.

Table III

| Compound acc. to | Inhibition of bacteria mixture in % with mg of active ingredient per liter of agar | | | |
|---|---|---|---|---|
| Example | 1000 | 500 | 100 | 50 |
| 3 |  | 100 | 90 | 50 |

Table III-continued

| Compound acc. to | Inhibition of bacteria mixture in % with mg of active ingredient per liter of agar | | | |
|---|---|---|---|---|
| Example | 1000 | 500 | 100 | 50 |
| 2 |  | 100 | 40 |  |
| 12 |  | 100 | 70 |  |
| 10 |  | 100 | 50 |  |
| 7 |  | 100 | 100 | 50 |
| 6 |  | 100 | 100 | 75 |
| 11 |  | 100 | 100 | 50 |
| 16 |  | 100 | 100 | 60 |
| 14 |  | 100 | 100 | 50 |
| 13 |  | 100 | 90 | 50 |
| 15 |  | 100 | 80 | 50 |
| A | 50 | 25 |  |  |
| B | 50 | 25 |  |  |

Tables I, II and III show the superior fungicidal and/or bactericidal action of the claimed compounds as compared with the comparative agents.

EXAMPLE IV:

Sugar beet plants in the 6-leaf state were strongly infected with conidia of the organism causing beet leaf spot (*Cercospora beticola*) and were placed, while dripping wet, into a climatic chamber having a temperature of 25° C. and a relative humidity of 100%. They remained there for 24 hours and were then taken to a green-house having a relative humidity of from 85 to 90% and a temperature in the range of from 24° to 25° C. After 7 days the plants were treated to the drip-off with an aqueous suspension of the compound of Example (14). The applied concentrations were 250, 120, 60 and 30 mg per liter of spraying liquid.

As comparative agent there was used compound C in the same concentrations.

Upon drying of the spraying liquid, the plants were taken back into a green-house. After an incubation period of 3 weeks the plants were examined for the infestation with beet leaf spot, and the findings were evaluated. The degree of damage was expressed in percent of attacked surface of the leaves, calculated on untreated infected control plants.

Table IV

| Compound acc. to | % of infestation with Cercospora with mg of active ingredient/l of spraying liquid | | | |
|---|---|---|---|---|
| Example | 250 | 120 | 60 | 30 |
| 14 | 0 | 0 | 3 | 5 |
| C | 0 | 3 | 5 | 10 |
| untreated infected plants |  | 100 |  |  |

EXAMPLE V:

Tomato plants of the type "Rheinlands Ruhm" in the 3-leaf state were treated to the drip-off with aqueous suspensions of the compounds mentioned in Table V. The applied concentrations were 500, 250, 120 and 60 mg of active ingredient per liter of spraying liquid. As comparative agent there was used compound D in the same concentrations. Upon drying of the spraying liquid, the plants were inoculated with a zoosporangia suspension of *Phytophthora infestans* and were placed for one day, while dripping wet, into a climatic chamber at a temperature of 15° C. and a relative humidity of 100%. Subsequently they were taken to a cool greenhouse having a temperature of 15° C. and a relative humidity of from 85° to 95° C.

After an incubation period of 7 days the plants were examined for the infestation with Phytophthora. The degree of damage was expressed in percent of attacked surface of the leaves, as compared with untreated infected control plants.

Table V:

| Compound acc. to Example | % of infestation with Phytophthora with mg of active ingredient/l of spraying liquid | | | |
|---|---|---|---|---|
| | 500 | 250 | 120 | 60 |
| 5 | 0 | 0 | 3 | 5 |
| 14 | 0 | 0 | 0 | 3 |
| D | 0 | 3 | 5 | 15 |
| untreated infected plants | | 100 | | |

EXAMPLE VI:

Vine plants in the 4-leaf state which had been cultivated from cuttings of the Müller-Thurgau type susceptible to Peronospora were treated to the drip-off with aqueous suspensions of the compounds of Examples (5) and (14). The applied concentrations were 500, 250, 120 and 60 mg of active ingredient per liter of spraying liquid. As comparative agent there was used compound E in the same concentrations as the test preparations.

Upon drying of the spraying liquid, the plants were inoculated with a zoosporangia suspension of *Peronospora viticola* and were placed, while dripping wet, into a climatic chamber having a temperature of 20° C. and a relative humidity of 100%. After 24 hours the infected plants were removed from the climatic chamber and were taken to a green-house having a temperature of 23° C. and a humidity of from 80 to 90%.

Following an incubation period of 7 days, the plants were moistened, were placed over night into the climatic chamber, whereupon the disease appeared. Subsequently the infestation was evaluated. The degree of damage was expressed in percent of attacked surface of the leaves, as compared with the untreated infected control plants, and has been shown in the following Table VI.

Table VI:

| Compound acc. to Example | % of infestation with Peronospora with mg of active ingredient/l of spraying liquid | | | |
|---|---|---|---|---|
| | 500 | 250 | 120 | 60 |
| 5 | 0 | 0 | 0 | 5 |
| 14 | 0 | 0 | 0 | 3 |
| E | 0 | 3 | 5 | 10 |
| untreated infected plants | | 100 | | |

EXAMPLE VII:

Of the 30% aqueous solution of N-3-hydroxypropyl-triazolidino-pyridazine-dione obtained according to Example 18, the following minimum inhibitor concentrations were ascertained in the test using nutrient medium plates against the microorganisms specified below:

*Aerobacter aerogenes;* 0.05%

*Bacillus subtilis;* 0.05%

*Pseudomonas aeruginosa;* 0.05%

*Saccharomyces cerevisiae;* 0.05%

*Alternaria cnsortiale;* 0.1%

*Aspergillus niger;* 0.1%

*Chaetomium globosum;* 0.05%

*Penicillium funiculosum;* 0.05%

We claim:
1. A triazolidino-pyridazine-dione of the formula

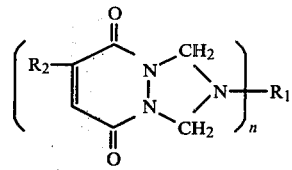

wherein n is an integer from 1 to 3,
$R_2$ is hydrogen or methyl, and wherein
(1) if n is 1, $R_1$ is an alkyl group having 1 to 18 carbon atoms, a cycloalkyl or methylcycloalkyl group having 5 to 8 carbon atoms, or a norbornylmethyl, hydroxyalkyl, alkoxyalkyl, or alkylmercaptoalkyl group each having 2 to 8 carbon atoms, or a phenyl, benzyl, or phenyl or benzyl group monosubstituted or di-substituted by a halogen, halogenalkyl, nitro, cyano, ($C_1$-$C_4$)-alkyl or ($C_1$-$C_4$)-alkoxy group; or
(2) if n is 2, $R_1$ is a bivalent saturated aliphatic hydrocarbon group having 1 to 36 carbon atoms or a bivalent saturated aliphatic hydrocarbon group having 1 to 36 carbon atoms mono-substituted or di-substituted by halogen or by ($C_1$-$C_4$)-hydroxyalkyl, ($C_1$-$C_4$)-alkoxyalkyl, or ($C_1$-$C_4$)-alkylmercaptoalkyl groups, or $R_1$ is a bivalent saturated cycloaliphatic hydrocarbon group having 5 to 8 carbon atoms or a bivalent saturated cycloaliphatic hydrocarbon group having 5 to 8 carbon atoms mono-substituted or di-substituted by a ($C_1$-$C_4$)-alkyl group, or $R_1$ is phenylene or phenylene monosubstituted or di-substituted by a ($C_1$-$C_4$)-hydroxyalkyl, ($C_1$-$C_4$)-halogenalkyl, ($C_1$-$C_4$)-alkoxyalkyl, ($C_1$-$C_4$)-alkylmercaptoalkyl, ($C_1$-$C_4$)-alkyl, nitro, cyano, or halogen group; or
(3) if n is 3, $R_1$ is a trivalent saturated aliphatic hydrocarbon group having 3 to 36 carbon atoms or a trivalent saturated aliphatic hydrocarbon group having 3 to 36 carbon atoms mono-substituted or di-substituted by halogen, or by a ($C_1$-$C_4$)-hydroxyalkyl, ($C_1$-$C_4$)-alkoxyalkyl, or ($C_1$-$C_4$)-alkylmercaptoalkyl group, or $R_1$ is a trivalent saturated cycloaliphatic hydrocarbon group having 5 to 8 carbon atoms or a trivalent saturated cycloaliphatic hydrocarbon group having 5 to 8 carbon atoms mono-substituted or di-substituted by a ($C_1$-$C_4$)-alkyl group, or $R_1$ is a trivalent benzene ring or a trivalent benzene ring mono-substituted or di-substituted by a ($C_1$-$C_4$)-hydroxyalkyl, ($C_1$-$C_4$)-halogenoalkyl, ($C_1$-$C_4$)-alkoxyalkyl, ($C_1$-$C_4$)-alkylmercaptoalkyl, ($C_1$-$C_4$)-alkyl, nitro, cyano, or halogen group.

2. A triazolidino-pyridazine-dione as claimed in claim 1, wherein n is 1 and $R_1$ is a ($C_1$-$C_{12}$)-alkyl, ($C_1$-$C_4$)-hydroxyalkyl, ($C_2$-$C_6$)-alkoxyalkyl, ($C_2$-$C_6$)-alkylmercaptoalkyl, or cyclohexyl group.

3. A triazolidino-pyridazine-dione as claimed in claim 1, wherein n is 2 and $R_1$ is a bivalent saturated ($C_1$–$C_{12}$)-aliphatic hydrocarbon group.

4. A triazolidino-pyridazine-dione as claimed in claim 1, wherein n is 2 and $R_1$ is a bivalent saturated ($C_1$–$C_6$) aliphatic hydrocarbon group or a bivalent saturated ($C_1$–$C_6$) aliphatic hydrocarbon group mono-substituted or di-substituted by a ($C_1$–$C_4$)-hydroxyalkyl, ($C_1$–$C_4$)-alkoxyalkyl, or ($C_1$–$C_4$)-alkylmercaptoalkyl group.

5. A triazolidino-pyridazine-dione as claimed in claim 1, wherein n is 3 and $R_1$ is a trivalent saturated ($C_3$–$C_9$)-aliphatic hydrocarbon group.

6. A triazolidino-pyridazine-dione as claimed in claim 1 wherein n is 1, $R_1$ is —$(CH_2)_3OH$, and $R_2$ is hydrogen.

7. A bactericidal and fungicidal composition comprising a bactericidally- and fungicidally-effective amount of a compound as in claim 1 in combination with a carrier therefor.

8. The method of protecting plants against bacteria and fungi which comprises applying to said plants, post-emergence, a bactericidally- and fungicidally-effective amount of a compound as in claim 1.

* * * * *